United States Patent [19]

Otterbacher

[11] Patent Number: 4,843,160
[45] Date of Patent: Jun. 27, 1989

[54] PREPARATION OF ALPHA-AMINOALKYLPHENOLS

[75] Inventor: Eric W. Otterbacher, Midland, Mich.

[73] Assignee: The Dow Chemical Company, Midland, Mich.

[21] Appl. No.: 656,377

[22] Filed: Oct. 1, 1984

[51] Int. Cl.$^4$ .................... C07D 295/00; C07C 87/28
[52] U.S. Cl. .................... 544/398; 564/280; 564/355; 564/384; 564/389; 564/390
[58] Field of Search ................ 544/398; 564/280, 355, 564/384, 389, 390

[56] References Cited

U.S. PATENT DOCUMENTS

| | | | |
|---|---|---|---|
| 2,013,052 | 9/1933 | Horsley | 564/384 |
| 2,363,134 | 11/1944 | McCleary | 564/384 |
| 2,858,312 | 10/1958 | Olin | 544/398 |
| 3,053,895 | 9/1962 | Kaeding | 260/574 |
| 3,384,667 | 5/1968 | Hamilton | 564/384 |
| 3,513,200 | 5/1970 | Biale | 260/583 |
| 3,657,244 | 4/1972 | Meutrup et al. | 564/362 |
| 3,784,640 | 1/1974 | Okumura et al. | 260/519 |
| 3,804,834 | 4/1974 | Meutrup et al. | 564/362 |
| 3,845,063 | 10/1974 | Balls | 260/293.84 |
| 3,969,410 | 7/1976 | Meutrup et al. | 564/362 |
| 4,017,543 | 4/1977 | Christy | 260/570.8 R |
| 4,322,530 | 3/1982 | Jachimowicz | 564/355 |

FOREIGN PATENT DOCUMENTS 103222  8/1981  Japan .

OTHER PUBLICATIONS

Basheeruddin et al., Chem. Abst. 92-688882.
Journal Amer. Chem. Soc., vol. 71, 3929–35, (1949).
Journal Organic Chem., vol. 37, 4343–5 (1972).
Organic Reactions, vol. 7, 303–41, (1942).
Derwent 2453k.
Chemical Abstracts 67:32443w.
Chemical Abstracts 68:77330u.
Chemical Abstracts 69:51793t.
Chemical Abstracts 72:31420c.
Chemical Abstracts 73:129326x.
Chemical Abstracts 74:64031w.
Chemical Abstracts 78:124885x.
Chemical Abstracts 82:367t.
Chemical Abstracts 87:84784r.
Chemical Abstracts 88:62956s.
Chemical Abstracts 90:132572f.
Chemical Abstracts 93:46178n.
Chemical Abstracts 95:80465e.
Chemical Abstracts 95:219891m.
Chemical Abstracts 96:7251y.
Chemical Abstracts 97:120482h.
Chemical Abstracts 99:1007p.

Primary Examiner—Donald G. Daus
Assistant Examiner—Cecilia Shen
Attorney, Agent, or Firm—Paul D. Hayhurst

[57] ABSTRACT

Prepare novel α-aminoalkylphenols by contacting an α-alkenylphenol and an amine under reaction conditions.

20 Claims, No Drawings

PREPARATION OF ALPHA-AMINOALKYLPHENOLS

BACKGROUND OF THE INVENTION

The present invention relates to the aliphatic amination of alkenylphenols. More specifically, it relates to the selective amination of the alpha carbon of α-alkenylphenols.

Alpha-aminoalkylphenols are useful as epoxy curing agents, chelating agents, intermediates to biologically active compounds, monomers, etc. Alpha-alkenyl aromatic compounds, such as styrene and α-methylstyrene, have been aminated on the aliphatic chain using a butyl-lithium catalyst to give products aminated on the beta aliphatic carbon atoms, in low to moderate yields. *J. Organic Chemistry*, V. 37, pp. 4243-5 (1972). However, neither α-alkenyl aromatic compounds, such as styrene and α-methylstyrene, nor α-alkenylphenols have been aminated previously to selectively yield the corresponding α-aminated products.

SUMMARY OF THE INVENTION

The present invention is a method for the selective preparation of novel α-aminoalkylphenols. These compounds are prepared by contacting an α-alkenylphenol and an amine under reaction conditions sufficient to produce the corresponding α-aminoalkylphenol. Surprisingly, the reaction proceeds readily under mild conditions to selectively produce the novel α-aminated phenols. The novel α-aminoalkylphenols are useful as epoxy curing agents, chelating agents, monomers for condensation polymers, precursors to isocyanates, and intermediates to biologically active compounds.

DETAILED DESCRIPTION OF THE INVENTION

The amines suitably employed in the process of the present invention include ammonia, primary amines and secondary amines. Polyamines can be employed. Examples of typical amines include 1-amino-2-hydroxyethane, 1,2-diaminoethane, piperazine, hydrazine, hydroxylamine and butylamine. Preferred amines are represented generally by the formula $HNRR_a$ wherein $R_a$ and R are independently H, lower alkyl, including cycloalkyl, or substituted lower alkyl. Additionally, R and $R_a$ taken together can form at least one ring, as in the case of piperazine. For the purposes of the present invention, the term "lower alkyl" refers to alkyl moieties having from 1 to about 10 carbon atoms. The term "substituted lower alkyl" refers to lower alkyl moieties having substitutents such as, for example, hydroxy, alkoxy, aryl, aryloxy, cyano and halo. Ammonia is the most preferred amine. The amine is employed in an amount which is sufficient to produce an α-aminoalkylphenol in the process of the present invention. For example, the amine can be employed in amounts which are larger or smaller than the stoichiometric amount. Typically, at least about one reactive equivalent of the amine is employed per reactive equivalent of the α-alkenylphenol.

The α-alkenylphenol employed in the process of the present invention is an ortho- or para-(α-alkenyl)-phenol. For the purposes of the present invention, the term "alpha" refers to the alkenyl carbon atom which is directly attached to the aromatic ring of the alkenylphenol reactant (α-alkenylphenol). Alpha-alkenylphenols must have at least one α-alkenyl moiety. Examples of typical α-alkenylphenols include 1-ethenyl-4-hydroxybenzene, 1-ethenyl-2-hydroxybenzene, 1-(1-methylethenyl)-4-hydroxybenzene, 1-(1-ethylethenyl)-4-hydroxybenzene, and the like. Preferred α-alkenylphenols are represented generally by the formula:

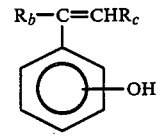

wherein $R_b$ and $R_c$ are independently H or lower alkyl; and wherein the hydroxy substituent is ortho or para to the alkenyl substituent. Preferably, $R_b$ is methyl and $R_c$ is H.

The process of the present invention can be conducted at any combination of temperature and pressure at which an α-aminoalkylphenol is produced. Typically, the contacting is conducted at a temperature of from about 0° C. to about 100° C. Preferably, the temperature is from about 20° C. to about 70° C. The typical process pressure ranges from about zero to about 10 atmospheres (about 0 to about 1,000 kPa) absolute.

An inert reaction medium optionally is employed in the process of the present invention. For the purposes of this invention, an inert reaction medium is a reaction medium which does not interfere with the selective α-amination of the α-alkenylphenol employed. Examples of suitable reaction media include water, alcohols, ketones, phenols, ethers, and polar aprotic solvents. Water is the preferred reaction medium. Typically, from about 0 to about 100 parts by weight of reaction medium are employed per weight part of α-alkenylphenol. The time required for the reaction varies according to the type and amount of reaction medium, the reactants, the temperature, and the pressure employed. Typically, the reaction takes from about 0.1 to about 1000 hours.

When the amine and the α-alkenylphenol are contacted under the reaction conditions described hereinabove an α-aminoalkylphenol is selectively produced. For the purposes of the present invention, the term "selectively" means that an α-aminoalkylphenol is produced in a selectivity, as defined hereinbelow, of at least about 70 mole percent. In the process of the present invention it is desirable to produce α-aminoalkylphenols selectively versus the β isomers. Thus, for the purposes of the present invention, selectivity is defined as selectivity to an α-aminoalkylphenol, and is calculated using the following equation:

% Selectivity = $(100)(Y)/(Y+Z)$ wherein Y is the molar quantity of α-aminoalkylphenol and wherein Z is the molar quantity of β-aminoalkylphenol in the reactor effluent. Advantageously, a selectivity of at least about 80 mole percent is achieved; preferably the selectivity is at least about 90 mole percent. Most preferably, no β-aminoalkylphenol is detectable in the reactor effluent using 60 MHz proton NMR (nuclear magnetic resonance) spectroscopy. The α-aminoalkylphenol product may be recovered by conventional means such as filtration or extraction.

Novel α-aminoalkylphenols are produced by the process described hereinabove. Examples of typical α-aminoalkylphenols include 2-amino-2-(4-hydroxyphenyl)-propane, 1-amino-1-(4-hydroxyphenyl)ethane, 1-amino-1-(2-hydroxyphenyl)ethane, 2-amino-2-(2-hydroxyphenyl)-propane, 2-(butylamino)-2-(4-hydroxyphenyl)propane, 2-(2-hydroxyethylamino)-2-(4-hydroxyphenyl)propane, 1-methyl-1-(4-hydroxyphenyl)ethylhydrazine, N,N'-bis[1-methyl-1-(4-hydroxyphenyl)ethyl]hydrazine, and N-[1-methyl-1-(4-hydroxyphenyl)ethyl]hydroxylamine. When polyamines such as 1,2-aminoethane are employed as the amine, bis(α-aminoalkylphenol)s can be produced by employing the proper stoichiometry. For example, 2 moles of 1-(1-methylethenyl)-4-hydroxybenzene can react with 1 mole of 1,2-aminoethane to form 1,2-bis[1-methyl-1-(4-hydroxyphenyl)ethylamino]ethane. Preferred α-aminoalkylphenols are represented generally by the formula:

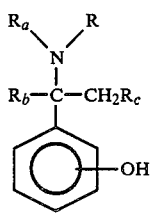

whereom R. $R_a$, $R_b$ and $R_c$ are as previously defined. Preferably, R, $R_a$, $R_b$ and $R_c$ are independently H or lower alkyl. Most preferably, $R_b$ is methyl; R, $R_a$, and $R_c$ are H; and the hydroxy moiety is para to the alkylamino moiety.

SPECIFIC EMBODIMENTS

The following examples and comparative experiments are given to illustrate the invention and should not be construed as limiting its scope. All parts and percentages are by weight unless otherwise indicated.

EXAMPLE 1

A 50-g portion of para-isopropenylphenol (1-(1-methylethenyl)-4-hydroxybenzene) and a 10 molar excess of 15N aqueous ammonia are heated and stirred at 50° C. for a period of about 1 day under autogeneous pressure (15–20 psig) in a closed heavywall glass bottle. The reaction mixture is then filtered. The filter cake is dried under vacuum over P₂O₅ giving an 88 percent yield of off-white solid product based on para-isopropenylphenol charged. The product is determined, via proton NMR, carbon-13 NMR, and high resolution mass spectrometry, to be 2-amino-2-(4-hydroxyphenyl)-propane. None of the β-aminated material, 1-amino-2-(4-hydroxyphenyl)propane is detectable by 60 MHz proton NMR.

EXAMPLE 2

A 0.10-g sample of 4-(1-methylethenyl)phenol is exposed to excess, gaseous ammonia for about one day at 50° C. After excess ammonia is purged, a quantitative yield of 2-amino-2-(4-hydroxyphenyl)propane is obtained. No 1-amino-2-(4-hydroxyphenyl)propane is detectable by 60 MHz proton NMR.

EXAMPLE 3

Two equivalents of p-isopropenylphenol are dissolved in about 5 parts of dioxane. One equivalent of 1,2-diaminoethane is added. The solution is heated at about 50° C. for about 13 days. The product is precipitated by pouring the reaction mixture into about 36 parts of acetonitrile. The mother liquors are removed. The solid is washed twice with acetonitrile and dried under vacuum. The product, which is a white solid of mp 141° C.-144° C., is determined by proton NMR, carbon-13 NMR, and high resolution mass spectrometry to be 1,2-bis[1-methyl-1-(4-hydroxyphenyl)ethylamino]ehtane. No β-aminated material is detectable by 60 MHz proton NMR.

EXAMPLE 4

A solution of about 5 parts of p-isopropenylphenol in about 14 parts of n-butylamine is heated at 50° C. for about 18 days. After removing the excess n-butylamine under reduced pressure, acetone is added. The resulting suspension is filtered. The filter cake is washed repeatedly with acetone, then dried under vacuum. The product, which is a white solid having a melting point of 125° C.-128° C., is determined by proton NMR and carbon-13 NMR to be 2-(butylamino)-2-(4-hydroxyphenyl)propane. No β-aminated material is detectable by 60 MHz proton NMR.

EXAMPLE 5

To a stirred mixture of 0.02 mole of p-isopropenylphenol, 0.06 mole of hydroxylamine hydrochloride and 20 ml of water, is added carefully 0.06 mole of NaHCO₃ resulting in CO₂ evolution. The mixture is heated and stirred at 60° C. for about 16 hours. The suspension is filtered. The filter cake is washed with water and dried. The product, which is obtained in 97 percent yield as a white powder of mp 156° C.-158° C., is determined by proton NMR to be N-[1-methyl-1-(4-hydroxyphenyl)ethyl]hydroxylamine. No β-aminated material is detectable by 60 MHz proton NMR.

COMPARATIVE EXPERIMENT 1

(Not an embodiment of the present invention)

A 10.0-g sample of 1,4-diisopropenylbenzene and a 10 molar excess of 15N aqueous ammonia are heated at 50° C. and stirred under autogenous pressure. At the end of about one day, neither 2-amino-2-(4-(1-methylethenyl)-phenyl)propane nor 1,4-bis(1-amino-1-methylethyl)-benzene is detectable by 60 MHz proton NMR. Thus, non-phenolic α-alkenyl compounds are not suitable for use as starting materials in the process of the present invention.

COMPARATIVE EXPERIMENT 2

(Not an embodiment of the present invention)

A 0.13-g sample of 3-(1-methylethenyl)phenol is exposed to excess, gaseous ammonia for two days at 50° C. No 2-amino-2-(3-hydroxyphenyl)propane is detectable by 60 MHz proton NMR. Thus, meta α-alkenylphenols are not suitable for use as starting materials in the process of the present invention.

COMPARATIVE EXPERIMENT 3

(Not an embodiment of the present invention)

A 0.10-g sample of 1-methoxy-4-(1-methylethenyl)-benzene is exposed to excess, gaseous ammonia for one day at 50° C. No 2-amino-2-(4-methoxyphenyl)propane is detectable by 60 MHz proton NMR. Comparative Experiment 3 confirms that the phenolic hydrogen is required of starting materials in the process of the present invention.

What is claimed is:

1. A process comprising contacting an ortho- or para- α-alkenylphenol and ammonia or a primary or secondary amine under reaction conditions to form an α-aminoalkylphenol.

2. The process of claim 1 wherein the α-aminoalkylphenol is represented by the following formula:

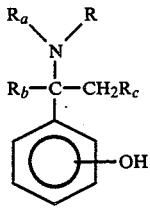

wherein $R_b$ and $R_c$ are independently H or lower alkyl; R and $R_a$ are independently H, lower alkyl, or substituted lower alkyl; or R and $R_a$ taken together are alkylene or heteroalkylene portions of a heterocycloalkyl moiety formed by R, $R_a$, and the N atom and α carbon atom of the preceding formula; and the —OH moiety is in the ortho or para position relative to the aminoalkyl moiety.

3. The process of claim 2 wherein $R_b$ is methyl, and $R_c$ is H.

4. The process of claim 3 wherein R and $R_a$ are H.

5. The process of claim 3 wherein $R_a$ is lowre alkyl.

6. The process of claim 1 wherein the selectivity to the α-aminoalkylphenol is at least about 80 mole percent.

7. The process of claim 3 wherein the hydroxyl moiety is in the para position relative to the aminoalkyl moiety.

8. The process of claim 1 wherein the amine comprises ammonia or hydroxylamine.

9. The process of claim 1 wherein the α-aminoalkyl phenol is represented by the following formula:

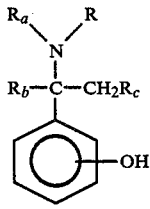

wherein $R_b$ and $R_c$ are independently H or lower alkyl; R is H, lower alkyl or substituted lower alkyl, and $R_a$ can be R, —NH$_2$, —CH$_2$CH$_2$OH, —OH or —CH$_2$CH$_2$NH$_2$, or R and $R_a$ taken together can be

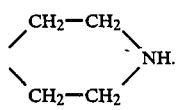

10. The process of claim 1 wherein the amine is a polyamine.

11. A process comprising contacting an ortho- or para- α-alkenylphenol and ammonia or a primary or secondary amine at a temperature of from about 0° C. to about 100° C. and under such other reaction conditions that an α-aminoalkylphenol selectively is produced.

12. The process of claim 11 wherein the contacting is in the presence of an inert reaction medium.

13. The process of claim 11 wherein the selectivity to the α-aminoalkylphenol is at least about 80 mole percent.

14. The process of claim 11 wherein the selectivity to the α-aminoalkylphenol is at least about 90 mole percent.

15. The process of claim 11 wherein the temperature is from about 20° C. to about 70° C.

16. The process of claim 11 wherein the α-alkenylphenol is represented generally by the formula:

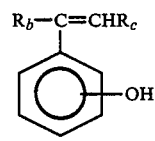

wherein $R_b$ and $R_c$ are independently H or lower alkyl; and wherein the hydroxy substituent is ortho or para to the alkenyl substituent.

17. The process of claim 11 wherein the amine is ammonia, 1,2,-diaminoethane, n-butylamine or hydroxylamine.

18. The process of claim 16 wherein $R_b$ is methyl and $R_c$ is H.

19. A process comprising contacting ammonia or hydroxylamine with p-isopropenylphenol under reaction conditions to selectively produce 2-amino-2-(4-hydroxyphenyl)propane or N-[1-methyl-1-(4-hydroxyphenyl)ethyl]-hydroxylamine.

20. The process of claim 19 wherein the contacting temperature is from about 0° C. to about 100° C.

* * * * *